United States Patent
Muzilla et al.

[11] Patent Number: 6,045,507
[45] Date of Patent: Apr. 4, 2000

[54] METHOD AND APPARATUS FOR ADAPTIVE COLOR FLOW OPTIMIZATION

[75] Inventors: David John Muzilla, Mukwonago, Wis.; Mir Said Seyed-Bolorforosh, Palo Alto, Calif.

[73] Assignee: General Electric Company, Milwaukee, Wis.

[21] Appl. No.: 09/169,785

[22] Filed: Oct. 9, 1998

[51] Int. Cl.[7] .................................. A61B 8/00; A61B 8/06
[52] U.S. Cl. ............................................ 600/443; 600/455
[58] Field of Search ....................................... 600/437, 443, 600/447, 454–456; 73/625–626; 367/138

[56] References Cited

U.S. PATENT DOCUMENTS

| | | | |
|---|---|---|---|
| 4,803,994 | 2/1989 | Burke | 600/442 |
| 4,819,652 | 4/1989 | Micco | 600/457 |
| 5,018,528 | 5/1991 | Morita et al. | 600/455 |
| 5,113,709 | 5/1992 | Pittaro | 600/447 |
| 5,458,129 | 10/1995 | Wheeler et al. | 600/454 |
| 5,482,046 | 1/1996 | Dietrich | 600/458 |
| 5,501,224 | 3/1996 | Shiki | 600/447 |
| 5,919,138 | 7/1999 | Ustuner | 600/443 |
| 5,995,450 | 11/1999 | Cole et al. | 367/138 |

*Primary Examiner*—Francis J. Jaworski
*Attorney, Agent, or Firm*—Dennis M. Flaherty; Christian G. Cabou; Phyllis Y. Price

[57] ABSTRACT

An ultrasound color flow imaging system is programmed to operate in an adaptive manner. The operational adjustments are made based on the system gain setting or the transmit packet size or both. Based on these operator inputs, the transmit burst length is adjusted for optimum operation. In addition, the transmit peak amplitude and the bandwidth of the receive filter are adjusted as a function of the burst length adjustment.

26 Claims, 4 Drawing Sheets

METHOD AND APPARATUS FOR ADAPTIVE COLOR FLOW OPTIMIZATION

FIELD OF THE INVENTION

This invention generally relates to ultrasound color flow Doppler imaging of fluid flow fields. In particular, the invention relates to a method and an apparatus for imaging blood flowing in the human body by detecting Doppler shifting of ultrasonic echoes reflected from the flowing blood.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase, shift translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

In standard color flow processing, a high pass filter known as a wall filter is applied to the data before a color flow estimate is made. The purpose of this filter is to remove signal components produced by tissue surrounding the blood flow of interest. If these signal components are not removed, the resulting velocity estimate will be a combination of the velocities from the blood flow and the surrounding tissue. The backscatter component from tissue is many times larger than that from blood, so the velocity estimate will most likely be more representative of the tissue, rather than the blood flow. In order to get the flow velocity, the tissue signal must be filtered out.

In the color flow mode of a conventional ultrasound imaging system, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilohertz range. A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by a beamformer.

For example, the traditional color firing sequence is a series of firings (e.g., tone bursts) along the same position, which firings produce the respective receive signals:

$F_1\ F_2\ F_3\ F_4\ \ldots\ F_M$ where $F_i$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point will be filtered to produce the respective difference signals:

$(F_1-F_2)\ (F_2-F_3)\ (F_3-F_4)\ \ldots\ (F_{M-1}-F_M)$ and these differences are input to a color flow velocity estimator.

One of the primary advantages of Doppler ultrasound is that it can provide noninvasive and quantitative measurements of blood flow in vessels. Given the angle $\theta$ between the insonifying beam and the flow axis, the magnitude of the velocity vector can be determined by the standard Doppler equation:

$$V = c f_d / (2 f_0 \cos \theta) \qquad (1)$$

where c is the speed of sound in blood, $f_0$ is the transmit frequency and $f_d$ is the motion-induced Doppler frequency shift in the backscattered ultrasound signal. The Doppler effect results in a time variation in the phase of the backscattered signal. This can be modeled as a phase modulation (or frequency modulation) system. The equations describing the signal-to-noise ratio for the phase modulation can be written to show how system performance is related to the bandwidth of the excitation signal.

Because blood has a very low backscatter coefficient, in medical ultrasound color flow imaging, it is desirable to improve flow visualization by optimizing the SNR and resolution. In medical ultrasound imaging, there are often situations where the peak power of a transmitted signal cannot be increased but the average power can, e.g., when system design limitations dictate the peak amplitude of the signal driving the transducer. Conventional color flow systems fire relatively long tone bursts to maximize the SNR.

There is a need for a method to adaptively control the system transmit and receive parameters to obtain the highest sensitivity together with the highest frame rate and best resolution.

SUMMARY OF THE INVENTION

The present invention is a method and an apparatus for adaptively controlling the system transmit and receive parameters to obtain the highest sensitivity together with the highest frame rate and best resolution. This method allows the overall color flow detection to be improved when operating under the condition of constant output power (due to regulatory, probe temperature or power supply limitation).

In accordance with the invention, an ultrasound color flow imaging system is programmed to operate in an adaptive manner. The operational adjustments are made based on the system gain setting or the packet size or both. Based on these operator inputs, the burst length is adjusted for optimum operation. In addition, the peak amplitude of the pulse and the bandwidth of the receive filter are adjusted as a function of the burst length adjustment.

DETAILED DESCRIPTION OF THE PREFERRED EMBODIMENTS

Figure 1:
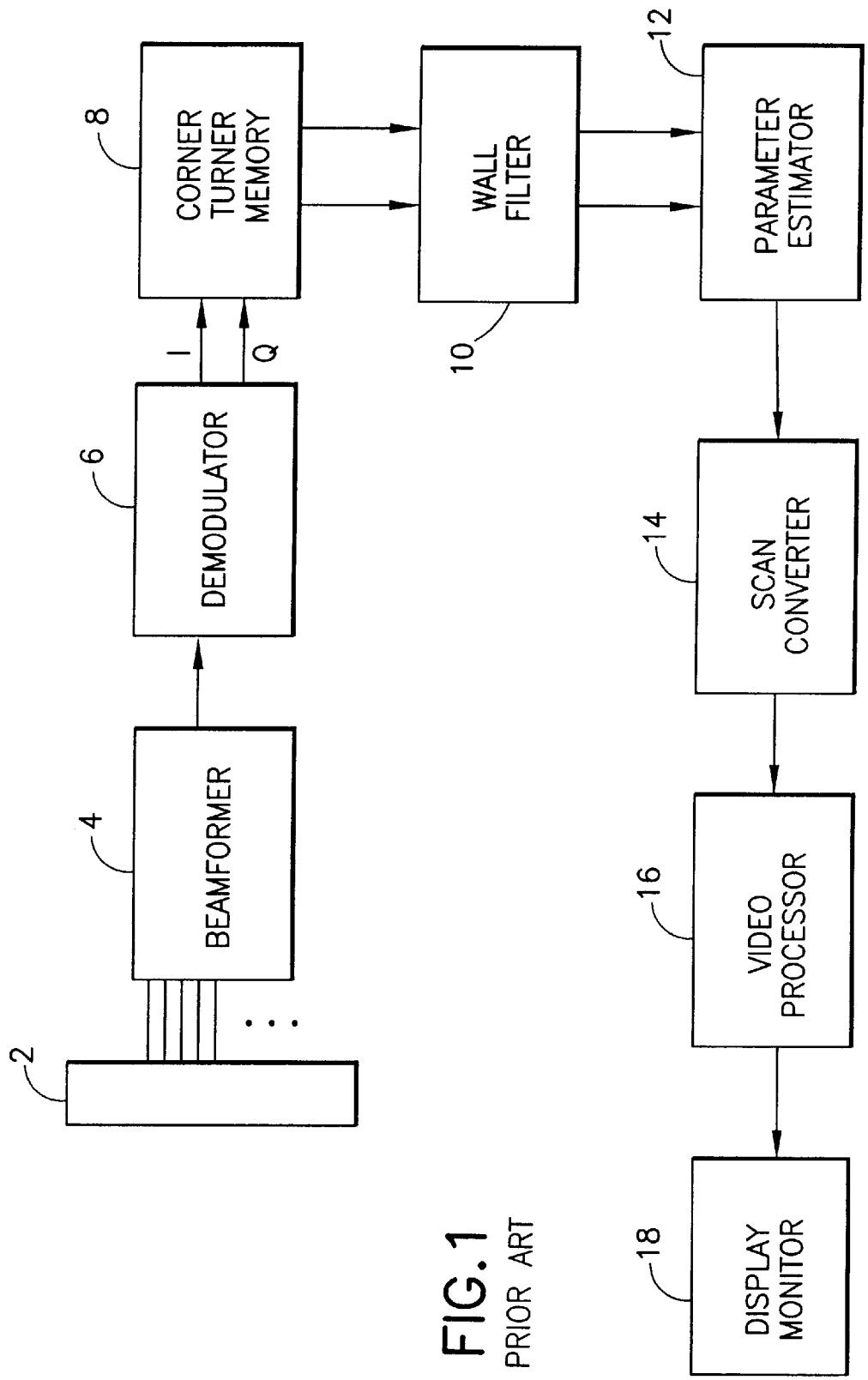
FIG. 1 is a block diagram showing the signal processing chain for a conventional color flow ultrasound imaging system.

Referring to FIG. 1, the basic signal processing chain for a color flow imaging system comprises an ultrasound transducer array 2, which is activated to transmit pulse sequences comprising tone bursts of length P which are fired repeatedly at the PRF. The return RF signals are detected by the transducer elements and received by the respective receive channels in the beamformer 4. The beamformer sums the delayed channel data and outputs a beamsummed signal, which is demodulated into in-phase and quadrature (I/Q) signal components by a demodulator 6. The I/Q signal components are stored in a corner turner memory 8, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through respective wall filters 10, which reject any clutter corresponding to stationary or very slow-moving tissue. The filtered outputs are then fed into a parameter estimator 12, which converts the range cell information into the intermediate autocorrelation parameters N, D and R(O). N and D are the numerator and denominator for the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} + Q_i Q_{i+1}) \quad (3)$$

where $I_i$ and $Q_i$ are the demodulated, basebanded input data for firing i, and M is the number of firings in the packet. R(O) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2} \quad (4)$$

A processor converts N and D into a magnitude and phase for each range cell. The equations used are as follows:

$$|R(T)| = \sqrt{N^2 + D^2} \quad (5)$$

$$\phi(R(T)) = \tan^{-1}\left[\frac{N}{D}\right] \quad (6)$$

The parameter estimator processes the magnitude and phase values into estimates of power, velocity and turbulence. The phase is used to calculate the mean Doppler frequency, which is proportional to the velocity as shown below; R(O) and |R(T)| (magnitude) are used to estimate the turbulence.

The mean Doppler frequency in hertz is obtained from the phase of N and D and the pulse repetition time T:

$$\bar{f} = \frac{1}{2\pi T}\tan^{-1}\left[\frac{N}{D}\right] = \frac{1}{2\pi T}(\phi(R(T))) \quad (7)$$

The mean velocity is calculated using the Doppler shift equation below. Since θ, the angle between the flow direction and the sampling direction, is not known, cos θ is assumed to be 1.0.

$$\bar{v} = \frac{\bar{f}}{f_o} \frac{c}{2\cos\theta} \quad (8)$$

Preferably, the parameter estimator does not calculate the mean Doppler frequency as an intermediate output, but calculates $\bar{v}$ directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions, R(O) and R(T) respectively. The exact autocorrelation functions are approximated by finite sums over the known data in the number of firings in a packet:

$$\sigma^2 = \frac{2}{(2\pi T)^2}\left[1 - \frac{|R(T)|}{R(0)}\right] \quad (9)$$

The mean value signal $\phi$ (R(T)) is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(O) indicates the amount of the returned power in the Doppler-shifted flow signal.

The color flow estimates are sent to a scan converter 14, which converts the color flow image data into X-Y format for video display. The scan-converted frames are passed to a video processor 16, which basically maps the video data to a display color map for video display. The color flow image frames are then sent to the video monitor 18 for display. Typically, either velocity or power are displayed alone or velocity is displayed in conjunction with either power or turbulence. System control is centered in a host computer (not shown), which accepts operator inputs through an operator interface (e.g., a keyboard) and in turn controls the various sub-systems.

Figure 2:
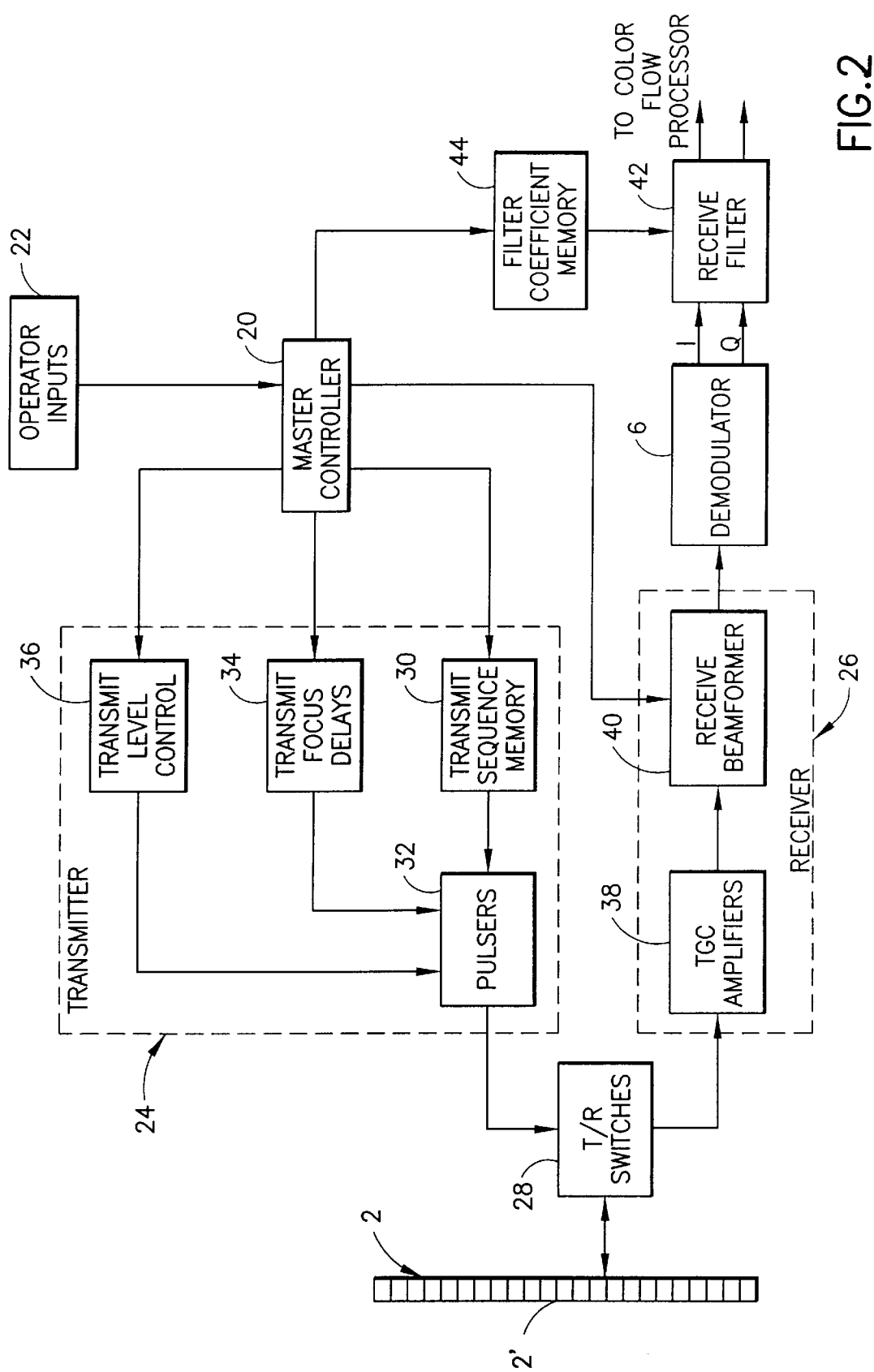
FIG. 2 is a block diagram showing the front end of a color flow ultrasound imaging system in accordance with a preferred embodiment of the invention.

The present invention may be incorporated in a system of the type depicted in FIG. 1 or other compatible color flow imaging systems. The preferred embodiment is shown in FIG. 2. System control is centered in a master controller 20 (or host computer), which accepts operator inputs through an operator interface 22 and in turn controls the various sub-systems. The master controller 20 also generates the system timing and control signals which are distributed via various control buses. The transducer array 2 consists of a plurality of separately driven transducer elements 2', each of which produces a burst of ultrasonic energy when energized by a pulsed waveform produced by a transmitter 24. The ultrasonic energy reflected back to transducer array 2 from the object under study is converted to an electrical signal by each receiving transducer element 2' and applied separately to a receiver 26 through a set of transmit/receive (T/R) switches 28. Transmitter 24 and receiver 26 are operated under control of master controller 20. A complete scan is performed by acquiring a series of echoes in which transmitter 24 is gated ON momentarily to energize each transducer element 2', and the subsequent echo signals produced by each transducer element 2' are applied to receiver 26. A channel may begin reception while another channel is still transmitting. The receiver 26 combines the separate echo signals from each transducer element to produce a single echo signal which is used to produce a line in an image on the display monitor.

Figure 3:
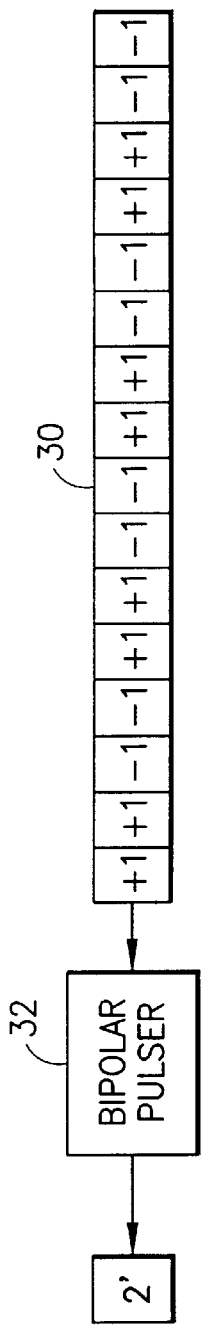
FIG. 3 is a block diagram depicting an exemplary transmit sequence for controlling a bipolar pulser connected to a transducer element.

In accordance with the preferred embodiment of the invention, adjustment of the length of the transmit pulses in each channel is implemented by programming a digital transmit sequence memory 30. Each transducer element 2' in the transmit aperture is pulsed by a pulse waveform output by a respective pulser 32 in response to a respective transmit sequence output to that pulser from the transmit sequence memory 30. The length of each pulse waveform (i.e., burst) is proportional to the number of bits in the respective digital transmit sequence. For example, FIG. 3 shows one such transmit sequence stored in transmit sequence memory 30 for driving a transducer element 2' with a burst of four cycles. In the case of bipolar pulsers, the +1 and −1 elements of each transmit sequence are transformed into pulses of opposite phase.

Under the direction of master controller 20, the transmitter 14 drives transducer array 2 such that the ultrasonic energy is transmitted as a directed focused beam. To accomplish focusing, respective time delays are imparted to the pulsers 32 by a transmit focus delay block 34, while respective peak pulse amplitudes are set by transmit level control block 36. The master controller 20 determines the conditions under which the acoustic pulses will be transmitted. With this information, the transmit focus delay and transmit level control blocks will respectively determine the timing and the amplitude of each of the transmit pulses to be generated by the pulsers 32. The pulsers 32 in turn send the transmit pulses to respective elements 2' of the transducer array 2 via the T/R switches 28, which protect the time-gain control (TGC) amplifiers 38 from the high voltages which may exist at the transducer array. By appropriately adjusting the transmit focus time delays in a conventional manner, an ultrasonic beam can be directed and focused at a transmit focal position.

The echo signals produced by each burst of ultrasonic energy reflect from objects located at successive ranges along each ultrasonic beam. Due to the differences in the propagation paths between a reflecting point and each transducer element, the echo signals will not be detected simultaneously and their amplitudes will not be equal. Receiver 26 amplifies the separate echo signals via a respective TGC amplifier 38 in each receive channel. The amplified echo signals are then fed to the receive beamformer 40, which imparts the proper time delays to the respective amplified echo signals. The receive time delays, like the transmit time delays, are provided under the control of the master controller. The receive time delays may be read out from look-up tables stored in random access memory. The receive beamformer 40 sums the time-delayed signals to provide an echo signal which accurately indicates the total ultrasonic energy reflected from a point located at a particular range along the ultrasonic beam.

The beamsummed receive signals are output to the demodulator 6, which forms the I and Q baseband components. These baseband components are bandpass-filtered in respective receive filters 42, which preferably take the form of finite impulse response filters. The filter coefficients are provided to the receive filters 42 from a filter coefficient memory 44 under the control of master controller 20. The bandwidth of the receive filters can be adjusted by changing the filter coefficients. The filtered outputs are then processed by the color flow processor, i.e., corner turner memory 8, wall filters 10 and a parameter estimator 12 shown in FIG. 1. As described above, the parameter estimator preferably includes a velocity estimator which estimates velocity as a function of the phase shift in the backscattered signals.

Figure 4:
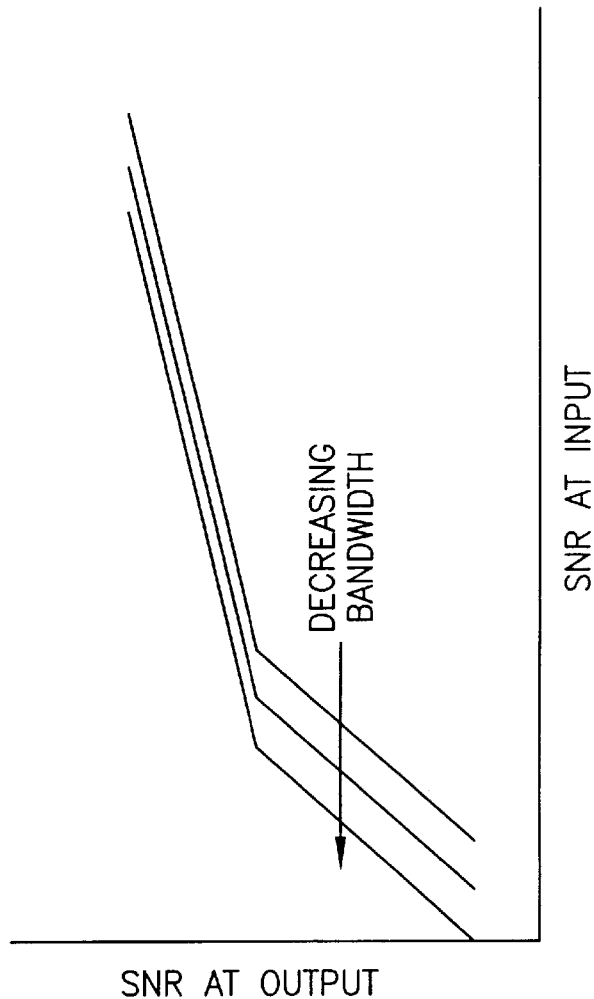
FIG. 4 is a graph showing the output SNR as a function of the input SNR for a phase-modulated signal.

The signal-to-noise ratio of the velocity estimator has a sharp knee as shown in FIG. 4. Above the knee point, a large increase in the estimator input SNR is required before the estimator output SNR would be significantly improved. At points below the knee point, a small increase in the estimator input SNR can result in a significant increase in the estimator output signal SNR. This implies that, once a certain input system level is reached, little gain in output SNR would result from increasing the peak input signal level further.

However, in a strong input SNR regime, it is advantageous to increase the number of cycles in the transmit waveform (i.e., increase the burst length) in order to improve the color flow detection estimate. This has the same effect as increasing the packet size. The increased packet size would increase the number of cycles used for the flow estimation for a given moving scatterer. However, with this scheme, instead of separating a pulse in the time domain in a number of packets, they are all transmitted at the same time. Although this degrades the resolution, it improves the detection capabilities of the color flow detector for the signals which are above the knee point of the SNR curve shown in FIG. 4. A closed-form solution can also be used which would show that, for an FM system, the SNR performance is a function of the input signal bandwidth. The smaller the bandwidth (longer burst or pulse length), the more accurate the estimate of the FM signal. Hence it is advantageous to have a waveform with lower peak voltage and longer pulse duration.

There is also a second effect which improves the color flow detection when using transmit pulses with a smaller peak voltage level. Due to the nonlinear harmonic generation of ultrasound in elastic media, every time a signal is transmitted, some of the energy moves to second and higher harmonics. The energy at the higher harmonic frequencies is not used in the process of color flow detection. In order to maintain the energy at the useful frequency band, it is important to either use a larger f-number or smaller peak drive voltage to limit the amount of energy at the higher harmonic levels. By reducing the amount of energy at the higher harmonic levels, the overall color flow detection capabilities can be improved.

There is a third advantage in using a longer pulse length. The integrated noise under the receive filter is reduced due to smaller receive filter bandwidth when imaging with longer burst length.

In accordance with one preferred embodiment of the invention, the burst length is adaptively adjusted depending on the system gain setting. The system would continuously monitor the system gain setting and then, in a linear or nonlinear manner, adjust the burst length to provide the optimum image quality. When the gain is low, indicating high SNR, the burst length is reduced to provide better resolution. When the gain is high, indicating low SNR, the burst length is automatically increased to provide optimum image quality. In both cases the peak drive voltage, or current, is adjusted to maintain a constant output power. The bandwidth of the receive filters can be adjusted to match the transmit waveform burst length by selection of appropriate filter coefficients.

In accordance with an alternative preferred embodiment, the burst length can be adjusted as a function of the packet size. If the packet size is reduced to achieve a faster frame rate, then the burst length can be increased, with reduced resolution, to compensate for the sensitivity loss due to smaller packet size. For larger packet size, a smaller burst length can be used to provide higher resolution. Under both conditions the output power is maintained at a constant level, by adjusting the peak drive voltage, or current, for different burst lengths. Similarly, the bandwidth of the receive filters can be adjusted to match the transmit waveform burst length.

In accordance with a further preferred embodiment, the above features can be combined in an adaptive manner such that the burst length is adjusted as a function of both the system gain setting and the packet size, both of which are set by the system operator.

Figure 5:
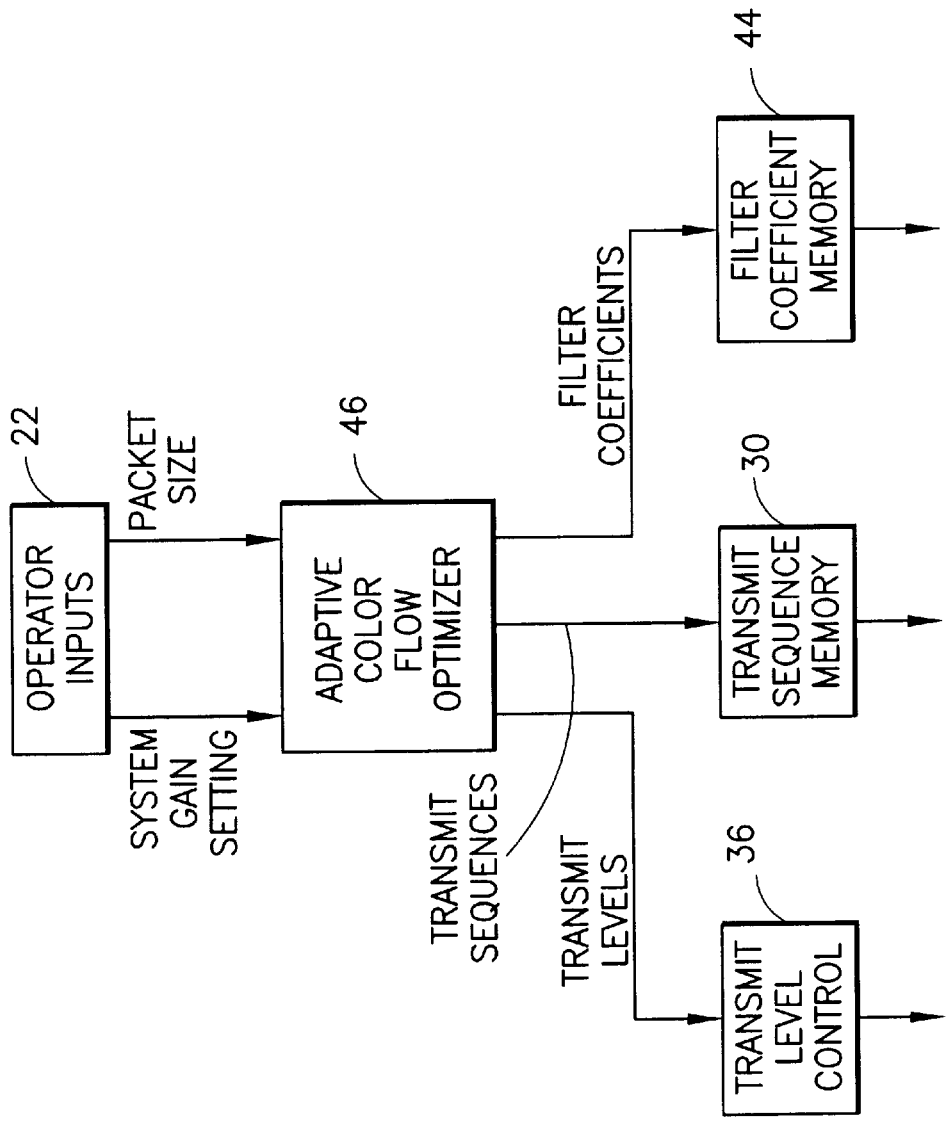
FIG. 5 is a block diagram showing an adaptive color flow optimizer in accordance with a preferred embodiment of the invention.

The preferred embodiment of the invention is generally depicted in FIG. 5. The system gain setting and the packet size are selected by the system operator and input to the adaptive color flow optimizer 46. Preferably, the adaptive color flow optimizer 46 takes the form of a software routine stored in the master controller. Alternatively, the optimizer can take the form of dedicated hardware. The adaptive color flow optimizer 46 outputs transmit sequences representing a transmit waveform burst length to the transmit sequence memory 30. The optimized burst length is dependent on one or both of the operator inputs: system gain setting and packet size. In addition, adaptive color flow optimizer 46 outputs transmit levels representing a peak transmit waveform amplitude to the transmit level control block 36 and filter coefficients representing a receive filter bandwidth to the filter coefficient memory 44. The peak transmit amplitude is adjusted to maintain a constant output power and is in this sense a function of burst length. Also the receive filter bandwidth is adjusted to match the transmit waveform burst length.

In one mode of optimizer operation, the burst length is increased in response to an increase in the system gain setting and is decreased in response to a decrease in the system gain setting, independent of the packet size. In another mode, the burst length is increased in response to a decrease in the packet size and is decreased in response to an increase in the packet size, independent of the system gain setting. In a third mode, the burst length is selected as a function of both the system gain setting and the packet size.

Phantom and body scans were performed in order to verify the enhanced color flow detection of the invention. Two transmit setups were compared. They both had the same amount of transmit power. However the pulse (burst) lengths were different by a factor of two (6 cycles versus 12 cycles). The peak amplitude was adjusted to have the same amount of output power in both cases. Phantom and abdomen images showed an improvement in the color flow sensitivity, i.e., the penetration was improved with lower background noise level in the setup with longer burst length. Hence the experimental results showed that for constant total power, it is advantageous to have longer pulse (burst) length with lower peak amplitude.

The foregoing preferred embodiments have been disclosed for the purpose of illustration. Variations and modifications of the concept of the invention will be readily apparent to persons skilled in the art. All such variations and modifications are intended to be encompassed by the claims set forth hereinafter.

We claim:

1. A system for transmitting ultrasound waves comprising:

an ultrasound transducer element;

a pulser for outputting an excitation waveform to said ultrasound transducer element for each of a plurality of transmit firings;

a transmit sequence source for outputting a transmit sequence to said pulser for each of said transmit firings;

an operator interface for selecting a number of transmit firings in a packet; and an adaptive color flow optimizer for determining an optimal transmit burst length which is a function of said number of transmit firings in said packet and controlling said transmit sequence source to output a transmit sequence suitable for producing an excitation waveform having said optimal transmit burst length.

2. The system as recited in claim 1, wherein said adaptive color flow optimizer determines an optimal transmit peak amplitude of said excitation waveform which is a function of said optimal transmit burst length, further comprising a transmit level control device for establishing said optimal transmit peak amplitude of said excitation waveform output by said pulser.

3. A method for transmitting ultrasound waves in an ultrasound imaging system, comprising the steps of:

selecting a number of transmit firings in a packet to be transmitted;

determining an optimal transmit burst length which is a function of said number of transmit firings in said packet; and for each of said transmit firings:

generating a transmit sequence suitable for producing an excitation waveform having said optimal transmit burst length;

generating said excitation waveform having said optimal transmit burst length in response to generation of said transmit sequence; and transducing said excitation waveform into an ultrasound wave.

4. The method as recited in claim 3, further comprising the steps of:

determining an optimal transmit peak amplitude of said excitation waveform as a function of said optimal transmit burst length; and for each of said transmit firings, generating a level control signal suitable for producing said excitation waveform having said optimal transmit peak amplitude.

5. The method as recited in claim 4, wherein said optimal transmit peak amplitude determining step is performed using a function which maintains a constant output power for varying transmit burst length.

6. The method as recited in claim 3, wherein said optimal transmit burst length determining step is performed using a function which decreases the transmit burst length in response to an increase in packet size and increases the transmit burst length in response to a decrease in packet size.

7. The method as recited in claim 3, further comprising the step of setting a system gain prior to said step of transducing said excitation waveform into an ultrasound wave, wherein said optimal transmit burst length is determined as a function of said gain setting.

8. A method for transmitting ultrasound waves in an ultrasound imaging system, comprising the steps of:

setting a system gain;

determining an optimal transmit burst length which is a function of said system gain setting; and for each of a plurality of transmit firings:
    generating a transmit sequence suitable for producing an excitation waveform having said optimal transmit burst length;
    generating said excitation waveform having said optimal transmit burst length in response to generation of said transmit sequence; and
    transducing said excitation waveform into an ultrasound wave.

9. The method as recited in claim 8, further comprising the steps of:
    determining an optimal transmit peak amplitude of said excitation waveform as a function of said optimal transmit burst length; and
    for each of said transmit firings, generating a level control signal suitable for producing said excitation waveform having said optimal transmit peak amplitude.

10. The method as recited in claim 9, wherein said optimal transmit peak amplitude determining step is performed using a function which maintains a constant output power for varying transmit burst length.

11. The method as recited in claim 8, wherein said optimal transmit burst length determining step is performed using a function which increases the transmit burst length in response to an increase in system gain and decreases the transmit burst length in response to a decrease in system gain.

12. An ultrasound imaging system comprising:
an operator interface for setting a system gain;
a transducer array comprising a multiplicity of transducer elements:
    burst length determining means for determining an optimal transmit burst length which is a function of said system gain setting;
    means for generating a transmit sequence suitable for producing an excitation waveform having said optimal transmit burst length;
    means for driving selected transducer elements forming a transmit aperture with said excitation waveform to form a beam focused in a transmit focal zone for each of a plurality of transmit firings forming a packet;
    a beamformer for forming a respective beamsummed signal from a respective set of signals transduced by selected transducer elements forming a receive aperture for each transmit firing in said packet;
    a processor for forming an image signal from said beamsummed signals; and
    a display device for displaying an image having an image portion which is a function of said image signal.

13. The system as recited in claim 12, further comprising:
peak amplitude determining means for determining an optimal transmit peak amplitude of said excitation waveform which is a function of said optimal transmit burst length; and
a transmit level control device for establishing said optimal transmit peak amplitude of said excitation waveform.

14. The system as recited in claim 13, wherein said peak amplitude determining means operates in accordance with a function which maintains a constant output power for varying transmit burst length.

15. The system as recited in claim 12, wherein said operator interface further comprises means for selecting the number of transmit firings in said packet, and said burst length determining means determines said optimal transmit burst length as a function of said selected number of transmit firings in said packet.

16. The system as recited in claim 12, wherein said processor comprises a receive filter having a plurality of inputs for receiving filter coefficients, further comprising:
    filter bandwidth determining means for determining an optimal receive filter bandwidth which is a function of said optimal transmit burst length; and
    means for supplying a set of filter coefficients to said receive filter inputs for configuring said receive filter to pass signals within said optimal receive filter bandwidth.

17. The system as recited in claim 12, wherein said burst length determining means operates in accordance with a function which increases the transmit burst length in response to an increase in system gain and decreases the transmit burst length in response to a decrease in system gain.

18. An ultrasound imaging system comprising:
a transducer array comprising a multiplicity of transducer elements:
    an operator interface for selecting the number of transmit firings in a packet to be transmitted;
    burst length determining means for determining an optimal transmit burst length which is a function of said selected number of transmit firings in said packet;
    means for generating a transmit sequence suitable for producing an excitation waveform having said optimal transmit burst length;
    means for driving selected transducer elements forming a transmit aperture with said excitation waveform to form a beam focused in a transmit focal zone for each transmit firing in said packet;
    a beamformer for forming a respective beamsummed signal from a respective set of signals transduced by selected transducer elements forming a receive aperture for each transmit firing in said packet;
    a processor for forming an image signal from said beamsummed signals; and
    a display device for displaying an image having an image portion which is a function of said image signal.

19. The system as recited in claim 18, wherein said burst length determining means determines said optimal transmit burst length in accordance with a function which decreases the transmit burst length in response to an increase in packet size and increases the transmit burst length in response to a decrease in packet size.

20. The system as recited in claim 18, further comprising:
peak amplitude determining means for determining an optimal transmit peak amplitude of said excitation waveform which is a function of said optimal transmit burst length; and
a transmit level control device for establishing said optimal transmit peak amplitude of said excitation waveform.

21. The system as recited in claim 20, wherein said peak amplitude determining means operates in accordance with a function which maintains a constant output power for varying transmit burst length.

22. The system as recited in claim 18, wherein said processor comprises a receive filter having a plurality of inputs for receiving filter coefficients, further comprising:

filter bandwidth determining means for determining an optimal receive filter bandwidth which is a function of said optimal transmit burst length; and means for supplying a set of filter coefficients to said receive filter inputs for configuring said receive filter to pass signals within said optimal receive filter bandwidth.

23. An ultrasound imaging system comprising:

a transducer array comprising a multiplicity of transducer elements:

an operator interface for setting a system gain and selecting the number of transmit firings in a packet to be transmitted;

a multiplicity of pulsers for outputting excitation waveforms to said transducer elements for each transmit firing in said packet;

a transmit sequence source for outputting a transmit sequences to said pulsers for each transmit firing in said packet;

an adaptive color flow optimizer for determining an optimal transmit burst length which is a function of at least one of the following: said system gain setting and said selected number of transmit firings in said packet, wherein said adaptive color flow optimizer controls said transmit sequence source to output a transmit sequence suitable for producing an excitation waveform having said optimal transmit burst length;

a transmit beamformer for controlling said pursers to drive selected transducer elements forming a transmit aperture with said excitation waveform to form a beam focused in a transmit focal zone for each of a plurality of transmit firings forming a packet;

a receive beamformer for forming a respective beamsummed signal from a respective set of signals transduced by selected transducer elements forming a receive aperture for each transmit firing in said packet;

a processor for forming an image signal from said beamsummed signals; and a display device for displaying an image having an image portion which is a function of said image signal.

24. The system as recited in claim 23, wherein said adaptive color flow optimizer determines an optimal transmit peak amplitude of said excitation waveform which is a function of said optimal transmit burst length, further comprising a transmit level control device for establishing said optimal transmit peak amplitude of said excitation waveform output by said pulsers.

25. The system as recited in claim 23, wherein said processor comprises a receive filter having a plurality of inputs for receiving filter coefficients, and said adaptive color flow optimizer determines an optimal receive filter bandwidth which is a function of said optimal transmit burst length, further comprising means for supplying a set of filter coefficients to said receive filter inputs for configuring said receive filter to pass signals within said optimal receive filter bandwidth.

26. A system for imaging ultrasound scatterers, comprising:

an operator interface for setting a system gain and selecting the number of transmit firings in a packet to be transmitted;

an ultrasound transducer array comprising a multiplicity of transducer elements;

a multiplicity of pulsers for outputting excitation waveforms to said transducer elements for each transmit firing in said packet;

a display monitor for displaying an image which is a function of an image signal;

a computer programmed to perform the following steps:
(a) determining an optimal transmit burst length which is a function of at least one of the following: said system gain setting and said selected number of transmit firings in said packet;
(b) providing a transmit sequence suitable for producing an excitation waveform having said optimal transmit burst length to each of said pulsers for each transmit firing in said packet;
(c) forming a respective beamsummed signal from a respective set of signals transduced by selected transducer elements forming a receive aperture for each transmit firing in said packet;
(d) processing said beamsummed signals to form an image signal; and
(e) displaying on said display monitor an image having an image portion which is a function of said image signal.

* * * * *